United States Patent
Picone

(10) Patent No.: US 7,345,286 B2
(45) Date of Patent: Mar. 18, 2008

(54) SYSTEM AND METHOD FOR RETRIEVING IONOSPHERIC PARAMETERS FROM DISK-VIEWING ULTRAVIOLET AIRGLOW DATA

(75) Inventor: J. Michael Picone, Falls Church, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/566,634

(22) Filed: Dec. 4, 2006

(65) Prior Publication Data

US 2007/0181817 A1    Aug. 9, 2007

Related U.S. Application Data

(60) Provisional application No. 60/748,230, filed on Dec. 2, 2005.

(51) Int. Cl.
*G01J 1/42* (2006.01)

(52) U.S. Cl. ................................ 250/372; 250/283

(58) Field of Classification Search ............... 250/365, 250/461.1, 545 R, 372
See application file for complete search history.

(56) References Cited

U.S. PATENT DOCUMENTS

| | | | |
|---|---|---|---|
| 6,714,868 B2 * | 3/2004 | Picone et al. ............... | 702/3 |
| 2005/0267685 A1 * | 12/2005 | Intriligator et al. ......... | 702/3 |
| 2006/0229813 A1 * | 10/2006 | Tobiska ...................... | 702/2 |

OTHER PUBLICATIONS

Picone et al., Investigation of ionospheric O+ remote sensing using the 834 angstrom-airglow, Journal of Geophysical Research, vol. 102, No. A2, p. 2441-2456, Feb. 1, 1997.*

* cited by examiner

*Primary Examiner*—Kiesha Rose
*Assistant Examiner*—Kiho Kim
(74) *Attorney, Agent, or Firm*—John J Karasek; Suresh Koshy

(57) ABSTRACT

The present invention provides a system and method for retrieving ionospheric parameters from dayside disk-viewing measurements of an ultraviolet emission within the upper atmospheric airglow. The invention may provide nowcasting and forecasting information of the ionosphere, which is important for ultraviolet communications.

1 Claim, 5 Drawing Sheets

Number Density of O+ ions (208)
Source Intensity of 83.4 nm Emissions (210)

SYSTEM AND METHOD FOR RETRIEVING IONOSPHERIC PARAMETERS FROM DISK-VIEWING ULTRAVIOLET AIRGLOW DATA

This Application claims the benefit of U.S. Provisional Application No. 60/748,230, filed Dec. 2, 2005, the entire disclosure of which is incorporated herein by reference.

BACKGROUND

The ionosphere is the ionized part of the atmosphere produced primarily by the absorption of solar radiation. It plays an important part in upper atmospheric electricity and forms the inner edge of the magnetosphere. It has practical importance because, among other functions, it influences radio wave propagation to distant places on the Earth. The influence extends across a wide range of radio frequency bands, well above the high frequency band, considered to be 3-30 MHz.

The F-region, also known as the Appleton layer, is approximately 120 km to 525 km above the surface of the Earth. Here extreme ultraviolet (UV) (10-100 nm) solar radiation ionizes atomic oxygen (O). The F-region is the most important part of the ionosphere in terms of high frequency (HF) communications. The F-region combines into one layer at night, and in the presence of sunlight (during daytime), it divides into two layers, the $F_1$ and $F_2$. The F-region is responsible for most skywave propagation of radio waves, and is thickest and most reflective of radio waves on the side of the Earth facing the sun. The amount of electrons in the F-region is the key parameter affecting radio communications. In the F-region, the amounts of electrons and $O^+$ ions are virtually identical. Accordingly, it is important to monitor the amount of atomic oxygen ions ($O^+$) in the F-region of the ionosphere to compensate for negative effects on such signals.

Satellite-borne remote sensing of the ionospheric F-region proposes disk-viewing dayside observations of 83.4 nm emissions by atomic oxygen ions ($O^+$). FIG. 1 illustrates such a system. In the figure a satellite 108 has a line of sight to the earth 106 along a vector 110, which passes through the top of F-region 102 and the bottom of F-region 104. By conventional methods, satellite 108 is able to detect a total of emissions by atomic oxygen ions ($O^+$) within and below the F-region or the portion of vector 110 that lies below 102. The spectroscopic notation for the dominant atomic oxygen ion ($O^+$) emission related to the ionosphere is "O II 83.4 nm," where the Roman numeral "II" specifies an emission from singly ionized atomic oxygen, or $O^+$. Emissions from a neutral atomic species would use the Roman numeral I. Here the term "disk-viewing" implies any measurement from above the Earth's surface in which the instrument line of sight intersects the surface of the Earth, for example, vector 110, even when the instrument field of view is not large enough to permit simultaneous imaging of the entire disk.

What would be more valuable for radio wave communications is an altitude profile $[O^+](z)$ of the amount of atomic oxygen ions ($O^+$) at each altitude z. In other words, in addition to the total amount of emission along vector portion 112, an altitude function $[O^+](z)$ of the $O^+$ number density along vector portion 112 would be valuable. A mapping of such altitude functions along an area of the earth would greatly enable HF communication systems to compensate for negative effects of atomic oxygen ions on HF and higher frequency signals.

Unfortunately, in the scientific community, there is a conventionally perceived insurmountable obstacle to disk imaging of the dayside ionosphere F-region using the 83.4 nm airglow along vector portion 112. It is conventionally accepted that such images are impossible to interpret because the information retrieval problem is severely under-determined (more variables than equations) and because the photons undergo resonant scattering in the F-region causing increased optical path length (reduced signal). To understand this problem more clearly, the production of 83.4 nm photons and the propagation of those photons through the F-region should be discussed in relation to the intensity of 83.4 nm emissions measured by the satellite instrument in a specific disc-viewed pixel.

As discussed above, ionospheric parameters define an altitude profile of $[O^+](z)$, where z is the altitude above earth at the geodetic latitude and longitude of the observation by a downward-pointing (or disk-viewing) space-borne spectrograph, spectrometer, or photometer, i.e., the F-region along vector portion 112. These parameters define an analytic profile, known as a Chapman layer:

$$[O^+](z) = N_{\max} \exp\left[\frac{1}{2}\left(1 - \frac{z - z_{\max}}{H} - \exp\left\{-\frac{z - z_{\max}}{H}\right\}\right)\right]. \quad (1)$$

FIG. 2 illustrates an exemplary Chapman layer or the F-region profile $[O^+](z)$ of the density of $O^+$ ions and the 83.4 nm source region as function of atmospheric altitude for a specific disc-viewed pixel. Notice that in FIG. 2, the vertical axis corresponds to the independent variable, z, and the horizontal axis represents the function $[O^+](z)$. As illustrated in the figure, the F-region 202 is bounded on top and bottom by dashed lines corresponding to 102 and 104 on FIG. 1. Area 204, above F-region 202, comprises more hydrogen ions ($H^+$) ions than oxygen ions ($O^+$). As such, the amount of $O^+$ ions is greatest at points in F-region 202, as represented by curve 208. Point 214 on curve 208 is the altitude, $z_{max}$, corresponding to the peak oxygen ion density $N_{max}$. Density curve 208 is a function of altitude, and is based on the altitude at which the $O^+$ number density peaks, the peak $O^+$ number density and the neutral atomic oxygen scale height, H, which determines the shape of the curve. As seen on the right-hand side of Equation (1) above, the second term in the parenthesis determines the decrease in $O^+$ number density as altitude increases, where $z > z_{max}$, and corresponds with the gradient of portion of curve 208 that is labeled 212. The third term in parenthesis is causing a rapid decrease in $O^+$ number density as altitude decreases, where $z < z_{max}$ corresponds with the gradient of portion of curve 208 that is labeled 216. The primary source of 83.4 nm emissions, curve 210, occurs primarily at altitudes below $z_{max}$. There the sun ionizes neutral atomic oxygen. Source region 210 extends below the F-region as shown. The satellite detector counts 83.4 nm photons that propagate upward from source region 210. This signal is reduced as the photons are scattered out of the instrument line of sight by the oxygen ions (O$^+$) in the F-region. This reduction is greater (the 83.4 nm signal is weaker) when the amount of O$^+$ is greater, that is, when N$_{max}$ (at point 214) is greater, or when H (label 212) is greater, causing the oxygen ion density curve to drop off more gradually with altitude z above z$_{max}$. The reduction is less (the 83.4 nm signal is stronger) when z$_{max}$ is lower, causing greater overlap of the F-region, 208, with the source region 210. Thus the measured signal depends directly on the altitude profile [O$^+$](z), which is characterized by N$_{max}$, z$_{max}$, and H. Note that H can be a function of altitude, z, introducing additional parameters into Equation (1) for the O$^+$ number density profile.

If the altitude, Z$_{max}$, of the O$^+$ number density peak, the peak O$^+$ number density, N$_{max}$, and the neutral atomic oxygen scale height, H, are known, then the F-region oxygen ion density profile [O$^+$](z) 208 is known, and the 83.4 nm intensity value along the vector 110 may be derived. With a derived intensity value and the detected 83.4 nm emission intensity, it would be possible to derive the altitude profile [O$^+$](z) of the amount of atomic oxygen ions (O$^+$). Hence, it would be possible to map a plurality of such altitude profiles over an area of the earth to greatly enable HF communication systems to compensate for effects of atomic oxygen ions on HF signals.

Unfortunately, conventional methods and systems are unable to accurately determine z$_{max}$, N$_{max}$, and H of the dayside ionosphere in the F-region using the 83.4 nm airglow along vector 110. Specifically, the retrieval problem is severely underdetermined; i.e., each line-of-sight observation (or each pixel of an image) along vector portion 112 produces one number, which contains partial information on the several parameters that are needed to specify realistically the associated altitude profile [O$^+$](z) of the O$^+$ number density. Denote by n$_m$ the number of ionospheric parameters required to estimate realistically the ionospheric altitude profile [O$^+$](z) within a specified altitude range and at a specified latitude, longitude, and time. As discussed above, the value of n$_m$ depends on the shape and peak value of [O$^+$](z) in the region of interest. For the ionospheric F-region, experimental studies have shown that n$_m \geq 3$. Without at least n$_n$−1 additional, relevant, independent numbers to supplement each disk-viewing airglow measurement, a unique quantitative estimate of [O$^+$](z) in the observed region is not possible. This obstacle has severely impeded the development of extreme ultraviolet disk-viewing systems for monitoring the dayside ionosphere or measuring dayside ionospheric parameters quantitatively.

What is needed is a method and system to accurately determine the ionospheric altitude profile [O$^+$](z) in the F-region using the 83.4 nm airglow along a vector from a satellite to the earth.

BRIEF SUMMARY

It is an object of the present invention to overcome the problems associated with conventional satellite disk-viewing dayside observations of the ionospheric F-region using 83.4 nm emissions by atomic oxygen ions (O$^+$).

The present invention removes the previously perceived insurmountable obstacle and verifies that, in fact, the 83.4 nm signal contains information on the peak ion density, the ionospheric scale height, and the height of the ionosphere O$^+$ number density peak. The invention adds background information to a value function that is minimized to compute a solution, thereby rendering the problem "determined," so that accurate maps of the peak ion density, the height of the ionosphere density peak, and/or scale height may be retrieved.

The present invention retrieves dayside ionospheric parameter maps from satellite-based disk images of the O$^+$ 83.4 nm radiance of the Earth. This provides detailed global or regional, three-dimensional ionospheric specification (current epoch) and can serve as input to global ionospheric forecast models.

The invention includes a method that includes detecting a first intensity of 83.4 nm airglow from singly charged oxygen ions (O$^+$) along a vector from Earth to a satellite above the ionosphere. The method additionally obtains: a first altitude at which the number density of singly charged oxygen ions (O$^+$) peaks in the F-region of the ionosphere along the vector from Earth to the satellite; a first peak singly charged oxygen ion (O$^+$) number density in the F-region of the ionosphere along the vector from Earth to the satellite; and a first atomic oxygen scale height in the F-region of the ionosphere along the vector from Earth to the satellite. The method additionally estimates: a second altitude at which the number density of singly charged oxygen ions (O$^+$) peaks in the F-region of the ionosphere along the vector from Earth to the satellite; a second peak singly charged oxygen ion (O$^+$) number density in the F-region of the ionosphere along the vector from Earth to the satellite; and a second atomic oxygen scale height in the F-region of the ionosphere along the vector from Earth to the satellite. The method additionally uses the estimated second altitude, the estimated second peak density and the estimated second atomic oxygen scale height to estimate an amount of singly charged oxygen ions (O$^+$) in the F-region of the ionosphere at points along the vector from Earth to the satellite. A second intensity of 83.4 nm airglow from singly charged oxygen ions (O$^+$) along the vector from Earth to the satellite is then estimated based on the estimated amounts of singly charged oxygen ions (O$^+$) in the F-region of the ionosphere at the points along the vector from Earth to the satellite. Then the method defines a generalized chi-squared function of the first altitude, the first peak density, the first atomic oxygen scale height, the estimated second altitude, the estimated second peak density, the estimated second atomic oxygen scale height, the first and the estimated second intensity. The generalized chi-squared function is then minimized by varying at least one of the estimated second altitude, the estimated second peak density and the estimated second atomic oxygen scale height to determine optimal estimates of the estimated second altitude, the estimated second peak density and the estimated second atomic oxygen scale height. Finally, the method includes determining the altitude profile of the amount of singly charged atomic oxygen ions (O$^+$) in the F-region of the ionosphere between the Earth and the satellite based on the optimal estimates of the estimated second altitude, the estimated second peak density and the estimated second atomic oxygen scale height.

Additional objects, advantages and novel features of the invention are set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF SUMMARY OF THE DRAWINGS

The accompanying drawings, which are incorporated in and form a part of the specification, illustrate an exemplary embodiment of the present invention and, together with the description serve to explain the principles of the invention. It is noted that the exemplary embodiment is drawn to iris recognition. In the drawings.

DETAILED DESCRIPTION

One exemplary embodiment of the present invention applies when the line of sight from a satellite is nearly perpendicular to the surface of the Earth, i.e, the angle from the vertical is sufficiently small that the ionospheric parameters to be measured (including regional averages) do not vary appreciably over the latitudinal and longitudinal range subtended by the vertical integration path.

The present invention solves the problem facing conventional systems discussed above by applying discrete inverse theory (DIT) for underdetermined problems. The key element is the addition of external information, which is called "a priori information" in the mathematical formation of DIT or "background data" in meteorological forecasting. The source of the background data field is an ionospheric model or additional external data (such as from an ionosonde or incoherent scatter radar) that are spatially and temporally near-coincident with the disk observation. The system also makes use of coincident measurements of airglow emissions from neutral species (i.e., atomic oxygen [O], molecular nitrogen [$N_2$], and molecular oxygen [$O_2$]), when available, or can use orbit-based total mass density data, which will always be available.

Figure 3:
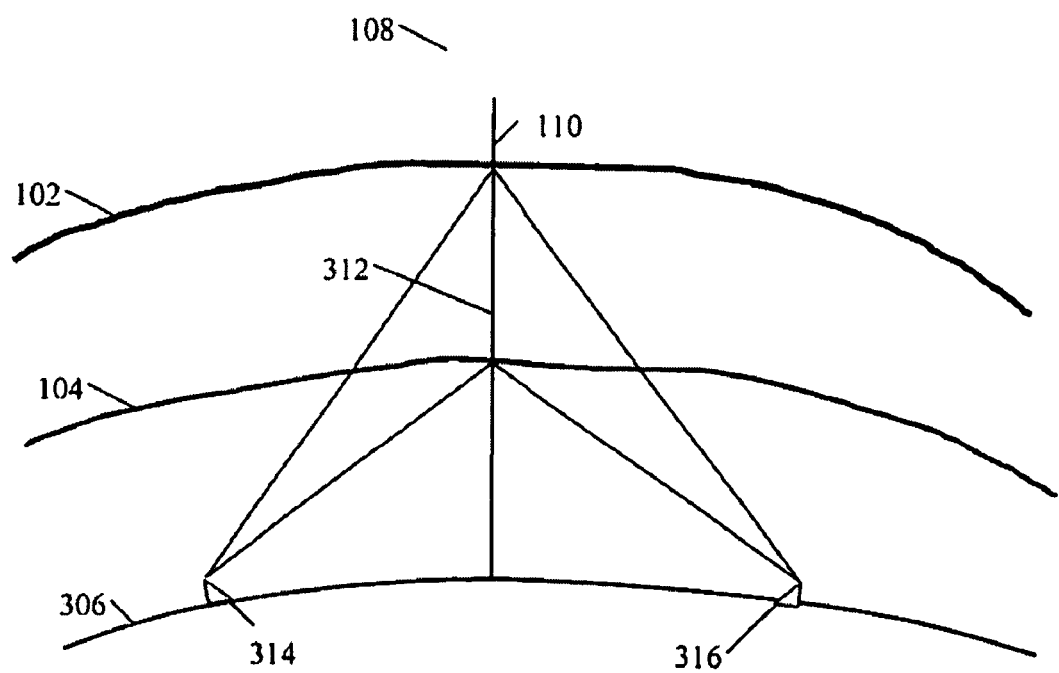
FIG. 3 shows illustrates a satellite-borne remote sensing system for disk-viewing dayside observations of 83.4 nm emissions by atomic oxygen ions ($O^+$) in accordance with the present invention.
Figure 4:
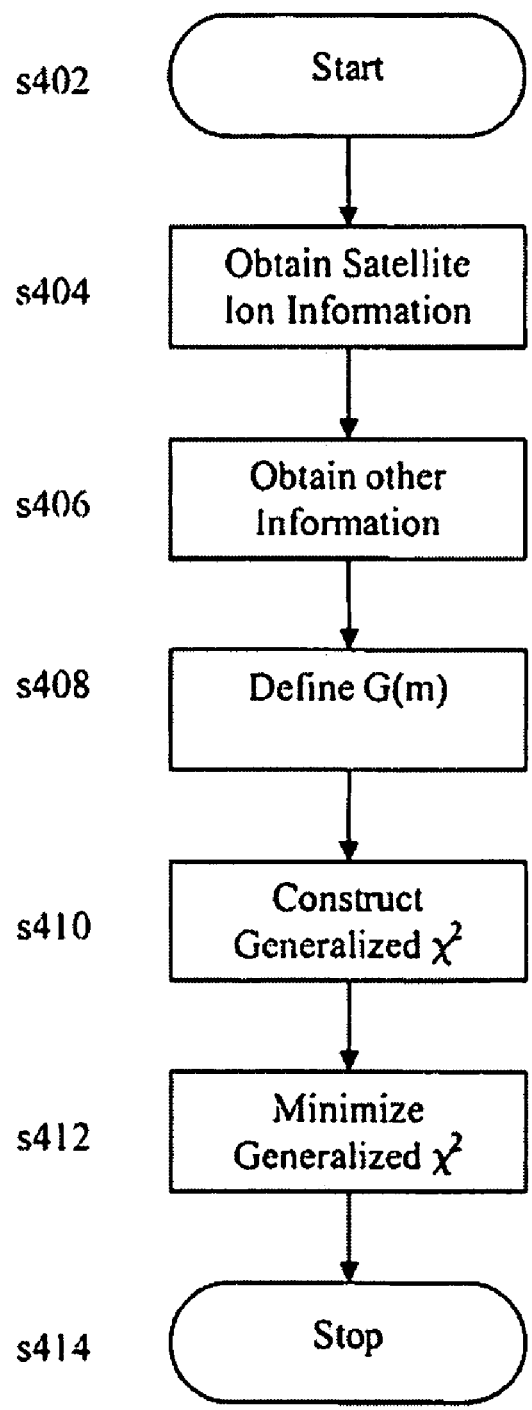
FIG. 4 is a logic flow chart of an exemplary method in accordance with the present invention.

A general description of an exemplary embodiment of the present invention will now be discussed with reference to FIGS. 3 and 4. In FIG. 3, a satellite 308 has a line of sight to the earth 306 along a vector 310 which passes through the top of F-region 302 and the bottom of F-region 304. By conventional methods, satellite 308 is able to detect a total of emissions by atomic oxygen ions ($O^+$) within the F-region or portion 312 of vector 310. Detectors 314 and 316 are operable to detect a priori information (such as from an ionosonde or incoherent scatter radar) and are spatially and temporally near-coincident with measurement from satellite 308. FIG. 4 is a logic flow chart of an exemplary method in accordance with the present invention.

As illustrated in FIG. 4, after the method starts s402, satellite ion information is obtained s404. In the exemplary embodiment, the satellite ion information is disk-viewed dayside information based on 83.4 nm emissions by atomic oxygen ions ($O^+$) that is obtained via satellite 308 along vector 310 in F-region 312. In a specific exemplary embodiment, the satellite ion information is an intensity, $d^o$, of 83.4 nm airglow from singly charged oxygen ions ($O^+$) that is obtained via satellite 308 along vector 310 in F-region 312. Any known method may be used to obtain $d^o$.

After the satellite ion information is obtained, the a priori information is obtained s406. In an exemplary embodiment, the a priori information is obtained by detectors 314 and 316 or other data sources. In a specific exemplary embodiment of the inventions the a priori information is: the altitude, $<Z_{max}>$, at which the number density of singly charged oxygen ions ($O^+$) peaks in the F-region of the ionosphere along vector portion 312; the peak singly charged oxygen ion ($O^+$) number density, $<N_{max}>$, in the F-region of the ionosphere along vector portion 312; and the (neutral) atomic oxygen scale height, $<H>$, in the F-region of the ionosphere along vector portion 312. In this exemplary embodiment, each of $<z_{max}>$, $<N_{max}>$ and $<H>$ are constant with respect to altitude z.

It should be noted that s404 and s406 are independent. As such, s404 and s406 may be executed in any order or at the same time.

Returning to FIG. 4, after the required information is obtained, a function $G(m)$ is defined s408. In accordance with an exemplary embodiment, an altitude, $z_{max}$, is estimated at which the number density of singly charged oxygen ions ($O^+$) peaks in the F-region of the ionosphere along vector portion 312; a peak singly charged oxygen ion ($O^+$) number density, $N_{max}$, is estimated in the F-region of the ionosphere along vector portion 312; and an atomic oxygen scale height, H, is estimated in the F-region of the ionosphere along vector portion 312. Estimated $z_{max}$, $N_{max}$ and H are used to estimate an amount of singly charged oxygen ions ($O^+$) in the F-region of the ionosphere at points along vector portion 312. The estimated amount of singly charged oxygen ions ($O^+$) in the F-region of the ionosphere at points along vector portion 312 is used to determine a corresponding estimated intensity, d, of 83.4 nm airglow from singly charged oxygen ions ($O^+$) along vector portion 312.

With detected intensity, $d^o$, obtained in S404, a generalized chi-squared function is created based on $<z_{max}>$, $<N_{max}>$, $<H>$, $z_{max}$, $N_{max}$, H, $d^o$ and d S410.

The generalized chi-squared function is then minimized by varying at least one of $z_{max}$, $N_{max}$, H to determine optimal estimates $Z_{max}$, $N_{max}$, H S412. Finally, the method includes determining the altitude profile $[O^+](z)$ of the amount of singly charged atomic oxygen ions ($O^+$) in the F-region along vector portion 312 based on the optimal estimates of $z_{max}$, $N_{max}$, H.

The invention will be described in greater detail in accordance with the exemplary embodiment below.

The present invention produces the ionospheric parameters, $z_{max}$, $N_{max}$, H, in order to define an altitude profile of $[O^+](z)$. The most useful generalization of Equation (1) has been the linear-H model, for which the parameter $H \equiv H(z) = H_0 + H_1 (z - z_{max})$ for $z > z_{max}$ and $H = H(z_{max})$ for $z \leq z_{max}$. The ionospheric parameters to be retrieved from the disk-viewing observations are $N_{max}$, $Z_{max}$, and $H_0$, and if selected, $H_1$, a small correction factor (~$10^{-2}$).

The present invention computes the optimal values of the vector of parameters m by minimizing the "generalized $\chi^2$", i.e., $\chi^2(m, d^o, \langle m \rangle)$:

$$\chi^2 = (d^o - G(m))^T ([cov\, d^o] + [cov\, G])^{-1} (d^o - G(m)) + \quad (2)$$
$$(m - \langle m \rangle)^T [cov\, m]^{-1} (m - \langle m \rangle),$$

where $d^o$ is a vector of observed intensity values for the appropriate airglow emission, i.e., 83.4 nm for dayside $O^+$, and cov $d^o$ is the covariance matrix of the observations. In Equation (2), the parameterized "forward model", denoted $$=d=G(m) \quad (3)$$

estimates theoretically (or numerically) the intensity observations. In Equations (2) and (3), the vector of ionospheric parameters to be retrieved is $m=[N_{max}, Z_{max}, H_0]$ (or $[N_{max}, z_{max}, H_0, H_1]$), and d is the vector of intensity estimates computed by the model G(m) for the instrument lines of sight and the location, time, and geophysical conditions of observation. The covariance matrix associated with the model is [cov G]. The vector m is the "model parameter vector" and consists of the parameters defining the space of possible forward model estimates. In discrete inverse theory, additional parameters are allowed within m, such as a parameter to scale the output intensity values from the forward model.

The vector $\langle m \rangle = [\langle N_{max}, \langle z_{max} \rangle \rangle, \langle H_0 \rangle]$ (or $[\langle N_{max}, \langle z_{max} \rangle \rangle, \langle H_0 \rangle, \langle H_1 \rangle]$) is a constant of a priori or "background" ionospheric parameter values derived from an assimilation (a combining) of external data sources or possibly from a physical model calculation appropriate for the location and time of the observed intensity values. If values from a physical model of the ionosphere are used to define $\langle m \rangle$, the model would preferably be an assimilative model that ingests recent or current data to develop a more accurate representation of the extant state of the ionosphere.

Also in Equation (2), the matrix cov m specifies the uncertainty and statistical variability of the background parameter vector $\langle m \rangle$. The user may define this matrix from a knowledge of the source of the selected value of $\langle m \rangle$. The value of cov m can also serve as a coarse tuning parameter whose value will ensure that the solution includes contributions from both the data $d^o$ and the background parameter values in the vector $\langle m \rangle$. The invention includes methods of tuning cov m for the particular observation set $\{d^o_i;$ index i ranging$\}$.

To compute a solution by minimizing $\chi^2$, the space of parameter values m may be systematically searched according to a standard algorithm, e.g., the Levenberg-Marquardt algorithm. Equation (2) may additionally be normalized by a factor 1/F, where F is the number of degrees of freedom, given by the number of data points minus the order of the parameter vector, m. Below, the notation "$\chi^2(m)$" is equivalent to $\chi^2(m, d^o, \langle m \rangle)$.

In standard "overdetermined" problems, the number of independent data points exceeds the order (or number of independent parameters) of m, and the definition of $\chi^2$ can exclude the second term of Equation (2), involving background parameter values $\langle m \rangle$. That is, the second term is often unnecessary to achieve convergence to a unique solution. In contrast, the present invention solves a severely underdetermined problem that has not previously been addressed in ionospheric remote sensing.

A dayside disk measurement of an 83.4 nm emission intensity, taken alone, contains insufficient information to determine the shape of the altitude profile $[O^+](z)$ of the emitting atomic or molecular species because the line of sight integral essentially sums (or averages) a complicated function of the species density profile over altitude z. However, the O II 83.4 nm emission is moderately optically thick in the ionospheric F-region because of resonant scattering of the photons by the $O^+$ ions in the F-region. That is, the F-region temporarily traps and re-emits the 83.4 nm photons, creating a secondary source that captures the shape of the profile $[O^+](z)$. On the other hand, the resonant scattering causes a reduction in the measured signal by scattering photons from the vector portion 312 at a rate that increases with the integrated $O^+$ density (i.e., the column density) from the observing system to the F-region. A key factor in the measured intensity is the degree of overlap of the F-region with the primary photon source, and hence, the disk measurement contains information on the height of the F-region (i.e., $z_{max}$) as well as the column density of $O^+$ (primarily the product $N_{max} \cdot H$).

In the simplest manifestation of this retrieval problem, one has a single disk-viewing observation of the selected emission, i.e., a dayside intensity value for the 83.4 nm emission by $O^+$ within the ionospheric F-region. The observing instrument produces this value by integrating the number of 83.4 nm photons over a prescribed length of time along the line-of-sight vector (unit vector $e^o$) from the instrument to the ground. For the present case, the vector $d^o$ in Equation (2) now equals $d^o$, a single element or scalar value. However, the vector m still contains a minimum of 3 unknown parameter values. Achieving a unique and meaningful solution thus requires at least two additional independent numbers that are related to the elements of m. If that requirement is met, the resulting solution for m, inserted into Equation (1), then gives the value of $[O^+](z)$, where the altitude vector is $z = z\, e_z$. The latter vector prescribes a distance from the ground to a height z along the unit vector $e_z$, which passes through the region of observation and is perpendicular to the Earth's surface. Note that the observed region does not extend to the ground, but at most coincides only with the F-region of the ionosphere.

Note further that all disk measurements within a region where the ionospheric parameters do not vary appreciably contain approximately the same information and, through averaging, serve primarily to reduce the statistical noise in the local disk-viewing intensity value from which information is to be retrieved. That is, the multiple measurements do not provide additional, independent information on the $n_m-1$ additional parameters required to specify the local ionospheric profile.

Figure 1:
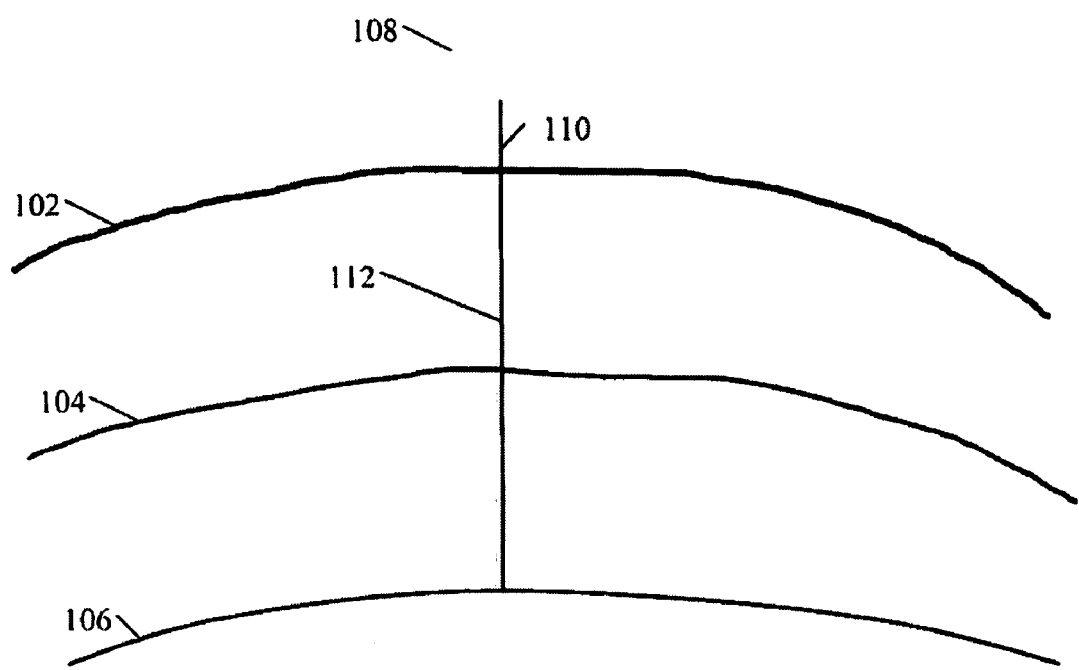
FIG. 1 illustrates a satellite-borne remote sensing system for disk-viewing dayside observations of 83.4 nm emissions by atomic oxygen ions ($O^+$)
Figure 2:
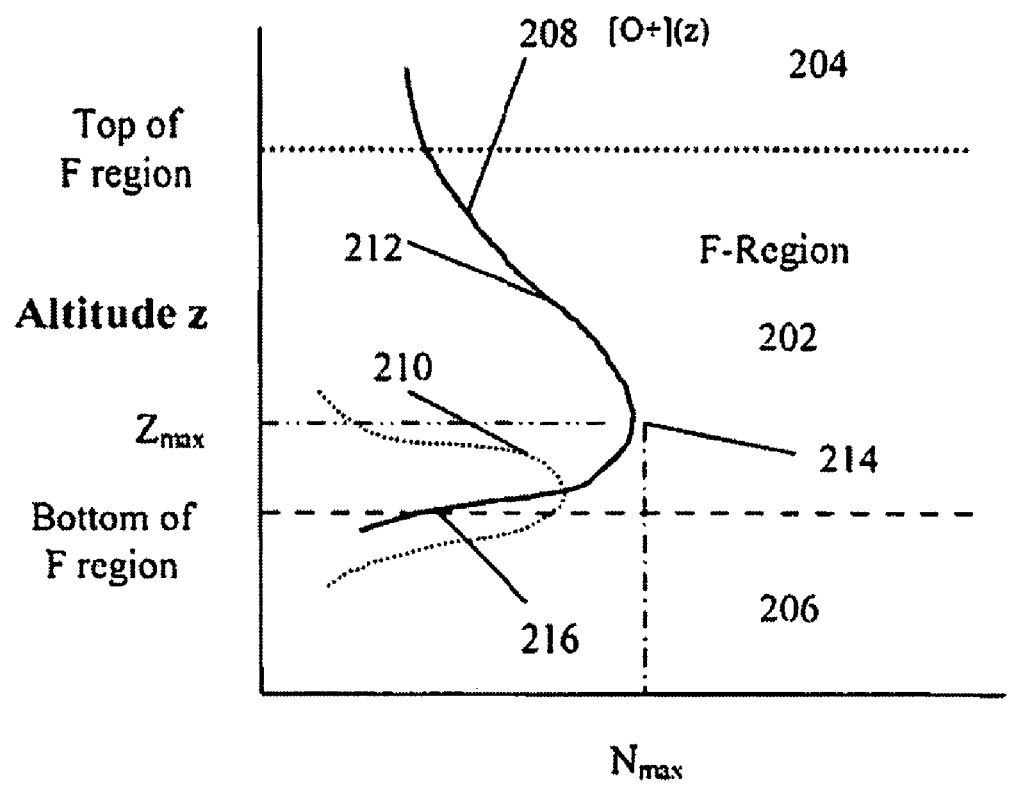
FIG. 2 illustrates an exemplary Chapman layer or the F-region profile $[O^+](z)$ of the density of $O^-$ ions and the 83.4 nm source region as function of atmospheric altitude for a specific disc-viewed pixel.

The schematic in FIG. 1 depicts both the disclosed algorithm to retrieve ionospheric parameters from disk observations of the upper atmospheric airglow and the system which implements the algorithm. Key components of an exemplary embodiment of a system in accordance with the present invention will now be described.

Downward-viewing data (denoted $d^o$ as above), i.e., a column integration of the relevant airglow emission is derived from either a near-Earth platform which views only a local region of the Earth's disk or from a pixel or contiguous set of pixels from a camera aboard a "deep space" platform (e.g., a geosynchronous satellite) which views the entire disk or a portion of the disk.

A priori ionospheric parameter values [a constant vector, denoted <m> in Equation (2)], are derived either from an ionospheric model or directly from external, coincident measurements containing independent information on at least two ionospheric parameters. The vector <m> contains estimates of at least $n_m-1$ the parameters $N_{max}$, $z_{max}$, and $H_0$ (and $H_1$, if selected) that determine the function $[O^+](z)$ in Equation (1).

A forward model then maps the model parameter vector, m, to an estimate of the data.

The generalized $\chi^2$, Equation (2), is minimized by searching the space of the forward model parameter vectors, {m}. An example of Such a minimization algorithm that may be used is the Levenberg-Marquardt algorithm.

As mentioned earlier, the core of the invention lies in combining the disk-viewing observations with background values (of the required ionospheric profile parameters) that are appropriate to the region of observation. Using this combined information to define a generalized $\chi^2$ function then renders the retrieval problem fully determined, with the solution defined by the minimum value of $\chi^2$.

Ionospheric disk/column data in accordance with an exemplary embodiment of the present invention will now be described.

Each disk-viewing, or column, intensity integration with time tag $t_i$ produces a single value of the intensity (number of photons counted over a prescribed time interval $\Delta t$), so that the vector $d^o(t_i)=d^o(t_i)$, a scalar value. The number, $d^o$, of photons counted in the time interval $\Delta t$, from counts/second may be converted to more convenient units commensurate with the forward model output, such as Rayleighs ($10^6/4\pi$ photons/cm$^2$/second/steradian). Alternatively, the forward model output intensity units may be converted to counts/second. Further the measurement or the forward model output may be adjusted to reflect the instrument sensitivity, dead-time, and resolution.

Thermospheric data in accordance with an exemplary embodiment of the present invention will now be described.

Thermospheric data includes additional data on the neutral upper atmosphere or "thermosphere," which extends from approximately 90 km above the Earth's surface to the "exobase" at approximately 500 km or higher. The height of the exobase depends on the stage of the extant solar cycle at the time of the observations. Such additional data may play a key role in the present invention by improving the predictions of the forward model. The major neutral species (molecular nitrogen [$N_2$], atomic oxygen [O], and molecular oxygen [$O_2$]) play two different roles in determining the dayside observations [denoted $d^o(t_i)$] of the ionospheric F-region at a specified latitude and longitude via the O II 83.4 nm airglow. First, ionization of neutral atomic oxygen within the thermosphere is the primary source of O II 83.4 nm photons that are measured by the observing system on the dayside. Second, the major neutral species absorb 83.4 nm photons following production and prior to detection.

For these reasons, the forward model requires values of the neutral species in the geographical region of observation to estimate properly the observed O II 83.4 nm intensity.

Quantitative information on the thermospheric total mass density is always available in the form of data on low-Earth orbits. In combination with a quantitative model of thermospheric composition and temperature, such orbit-based total mass density data translate into improved global information on the concentrations of the major neutral species and therefore improve the forward intensity model for dayside O II 83.4 nm observations. The present invention may incorporate a user's preferred method of combining the thermospheric data and model. Further, a data assimilation code or an ionospheric model may incorporate the orbit-based total mass density values into its internal model of the thermosphere. The particular method of combining a thermospheric model with external data depends on the particular thermospheric model and is known to those of skill in the art.

In addition, airglow measurements by the disk-viewing upper atmospheric observing system can include emissions from the major (neutral) species within the thermosphere. Such observations detect airglow from the middle and upper thermosphere (altitudes above 110 km). Standard algorithms are available to retrieve information on the ratio of the atomic oxygen column density to that of molecular nitrogen, based on measurements of the column emission rates (disk-viewing intensities) of an atomic oxygen emission (usually O I 135.6 nm) and a molecular nitrogen Lyman-Birge-Hopfield vibrational band. The method of combining a thermospheric model with measured column emission ratios or column density ratios is model-dependent and is also known to those of skill in the art.

A forward model and covariance in accordance with an exemplary embodiment of the present invention will now be described.

A parametric forward intensity model predicts the dayside O II 83.4 nm intensity along al given line of sight and for a given ionospheric parameter vector m and observation latitude longitude, and time $t_i$ (i.e., local time and day of year). This model defines G(m) in Equations (2)-(3) and is essential to the parametric function $\chi^2(m)$ in Equation (2). An acceptable and established formulation of the forward model for the dayside O II 83.4 nm emission is known to those of skill in the art.

In general, the forward model covariance matrix, cov G, in Equation (2) is known. Further, cov G for the particular problem of UV remote sensing of the ionosphere is additionally known. The matrix cov G accounts for uncertainties in the fixed internal parameters (e.g., cross sections) defining a particular forward model and often accounts for the bias of the model intensity value, $d(t_i)$ for an observation at time $t_i$. The present invention accepts any realistic user-defined forward model and covariance matrix. Given G(m) and cov G, a standard nonlinear minimization algorithm can search the space of values $\chi^2(m)$, spanned by m and implied by G(m) and cov G, for a numerical solution $m=m^s$ such that $\chi^2(m^s)$ is sufficiently near a global minimum.

An exemplary sequence of operations in accordance with the present invention will now be described.

A system in accordance with the present invention may be preliminary tuned. Specifically, using sample values of $d^o(t_i)$, the system may be tuned by testing the value of cov m to ensure that the observations properly influence the solution.

After the optional tuning for each observation, indexed by "i" exemplary sequence of operations includes: 1) specifying the datum and observing parameters; 2) computing the background data input $<m>_i$; 3) selecting an appropriate value of cov m; 4) defining $\chi^2(m. d^o(t_i), <m>_i)$; 5) minimizing $\chi^2(m. d^o(t_i), <m>_i)$; and 6) outputting a solution: $m^s_i$.

The specified datum and observed parameters include $t_i$, the time tag of $i^{th}$ datum, which may include a date. Additionally included is $d^o(t_i)$, the $i^{th}$ datum, in units consistent with forward intensity model (usually average counts/second or Rayleighs). This value can actually be the average of the independent observations within a selected geographical region (e.g., a cluster of pixels), especially if the size of the region is smaller than the scale of variation of the F-region parameters. Further included is the variance of the observation, con $d^o$=cov $d^o$ (a scalar), and the variance cov G of the forward intensity model. Still further are included coordinates (latitude, longitude, altitude) of the instrument and observation region. Finally, $e^o$, the observation vector (line-of-sight from instrument to ground) is included.

A first exemplary background data input $<m>_i$ computation will be described, wherein $<m>_i$ is produced from a physical or assimilative model $[O^+]$ field (over latitude, longitude, and altitude) for time $t_i$. For example, first a 3-dimensional model density field is interpolated to a grid of positions along the instrument line of sight corresponding to $d^o(t_i)$. This gives a profile $[O^+]^{mod}(s^o)$, of $O^+$density values at a set $s^o$ of $N^o$ locations $\{s^o_k;$ index $k=1, 2, \ldots, N^o\}$ along $e^o$. Then, by varying $N_{max}$, $z_{max}$, and $H_0$ (and if selected, $H_1$) in Equation (1), the function $[O^+](z)$ is fit to $[O+]^{mod}(s^o)$, where $z=\{z_k; k=1, 2, \ldots, N^o\}$ is a set of locations along a user-selected altitude vector near or intersecting the instrument line of sight $e^o$. Final (fit) parameter values are determined for observation "i": $N^1_{max}$, $z^f_{max}$, and $H^f_0$ (and if selected, $H^f_1$)$\rightarrow <m>_i$.

In another exemplary background data input $<m>_i$ computation, averaging, statistical methods, interpolation, or discrete inverse theory (fitting), may be used to assimilate (combine into a common framework) independently measured, near-coincident ionospheric data are from one or more sources, e.g., ionosonde.

In another exemplary background data input $<m>_i$ computation, independently measured, near-coincident [i.e., date, time, location] ionospheric data may be ingested from one or more sources into an assimilative model, and $<m>_i$ is computed.

In yet another exemplary background data input $<m>_i$ computation, a physical model $[O^+]$ field may be combined with independently measured, near-coincident ionospheric data to assimilate (combine into a common framework) independently measured, near-coincident ionospheric data are from one or more sources, e.g., ionosonde.

Once the background data input $<m>_i$ is computed an appropriate value of cov m is selected.

Selecting cov m to tune the method of the exemplary embodiment will first be described. The variables con $d^o$+cov G and cov m control the relative importance of the two terms in $\chi^2$ (m, $d^o(t_i)$, $<m>_i$), that is, the relative influence of the datum $d^o(t_i)$ and the background parameter values $<m>_i$ on the final solution $m^s_i$ (i.e., the ionospheric parameters), for each datum "i". A system in accordance with an exemplary embodiment of the present invention can therefore choose the elements of cov in to ensure that the background vectors $\{<m>_i,$ i ranging over the set observations$\}$ do not dominate the solution and that the information present in the observations, $\{d^o(t_i)\}$ is fully exploited. A value of cov m may be selected by trial and error, by qualitative interpretation of a series of tests with different values of cov m, or by testing systematically.

A systematic selection (coarse tuning) of cov m will now be described, wherein systematic method will use only a diagonal matrix cov m. Further the elements [cov m]$^c_{jj}$ for j=1, 2, . . . , $n_m$, will be chosen (as designated by the superscript "c"), through inversion of an ensemble of test data samples, labeled by superscript $\alpha=1, 2, \ldots, A$, where A is the number of data samples. These inversions will test a range of values $\{$[cov m]$_{jj}^p$; j=1, 2, . . . , $n_m$; p=1, 2, . . . , P$\}$ where p indexes a number "P" of test matrix element sets. The notation for component j of the a priori parameter vector, for a given test datum labeled by $\alpha$, is $<m_j>^\alpha$.

The exemplary test procedure discussed immediately above includes the following six steps.

First a set of "ratios," $\{f_j^p\}$, are selected from which to compute an ensemble of test covariance matrix element values, [cov m]$_{jj}^p$, according to the Equation.

$$f_j^p = ([cov\ m]_{jj}^p)^{1/2} <m_j>^{rep}, \quad (4)$$

where $<m_j>^{rep}$ is a representative value of the $j^{th}$ component of the background parameter vector. By considering the range of values observed historically, $<m_j>^{rep}$ may be defined. Alternatively, if $<m_j> \neq 0$, $<m_j>^{rep}$ could be set equal to max $\{<m_j>^\alpha;$ $\alpha$ ranging over test data samples$\}$, where the background data values labeled by $\alpha$ correspond to the observing conditions for each test datum, $d^o(t_\alpha)$. The discussion below assumes that the ratios $f_j^p$ increase monotonically with index p=1, 2, . . . , P. The range of values $f_j^p$ should be sufficiently large to permit a "near-optimal" selection as outlined in the following steps.

Second, the data, labeled by superscript $\alpha$, may be inverted for each background covariance matrix, labeled by superscript p.

Third, for each ratio p, test datum $\alpha$, and component j of the diagonal matrix [cov m]$_{jj}^p$, the data influence measure $$I_j^{p\alpha} = \left| \frac{(m_j^s)^{p\alpha} - <m_j>^\alpha}{<m_j>^\alpha} \right|, \quad (5)$$

may be computed, where superscript "s" denotes the retrieval solution for given p and $\alpha$.

Fourth, for each value of parameter index j and ratio p, a representative value, denoted $I_j^p$, may be selected of the data influence measure from the range of results $\{I_j^{p\alpha}; \alpha \text{ ranging}\}$ derived from the test data. A preferred criterion (e.g., median value) may be applied. Alternatively, the average influence measures $\{I_j^p; j, p \text{ ranging}\}$ may be computed, where $$I_j^p = \frac{1}{A}\sum_{\alpha=1}^{A} I_j^{p\alpha}. \quad (6)$$

Fifth, for each j, using the set $\{I_j^p; p \text{ ranging}\}$, a "near-optimal" value p(j) of the index p may be selected such that the influence $I_j^p$ is a maximum under the constraint $$I_j^{p(j)} - I_j^{p(j)-1} > \epsilon(I_j^{p(j)-1} - I_j^{p(j)-2}), \quad (7)$$

i.e., that the successive difference is also increasing, where $\epsilon$ is a constant selected by the user to define the minimum acceptable increase in the data influence.

Sixth, for the retrieval of ionospheric parameters, the $(j,k)_{th}$ element of the "chosen" covariance matrix of the background parameter values is then given by $$[\text{cov } m]^c_{jk} = \delta_{jk} f_j^{p(j)} <m_j>^{rep}, \quad (8)$$

where $<m_j>^{rep}$ is the $j^{th}$ component of the previously defined representative background parameter vector. The set of elements indexed by all pairs (j,k) then define the chosen covariance matrix of the background parameter vector $<m>$.

The objective of this procedure and particularly the fifth step discussed in paragraph [0074] is to determine the ratio $f_j^{p(j)}$ (for each parameter, labeled by j) such that the data produce a solution that differs from the background parameter values according to the information content of the data. This procedure selects the ratio for parameter j to produce the largest possible data influence while maintaining the smallest possible value of $[\text{cov } m]_{jj}$. An alternative criterion may be selected for the fourth step to estimate the influence $I_j^p$ and may use the value of $\epsilon$ to customize the size of the ratio $f_j^{p(j)}$ and therefore the size of $[\text{cov } m]^c_{jj}$.

A variant on the above-discussed exemplary test procedure discussed immediately includes a more compute-intensive procedure, wherein use $<m_j>^\alpha$ in place of $<m_j>^{rep}$ in Equations (4) and (8). This would produce a covariance matrix that changes with the observing conditions (identified by $\alpha$), i.e., $[\text{cov } m]^c_{jj}{}^{p\alpha}$, and requires the following substitutions in the above Equations:

(a) $[\text{cov } m]_{jj}^{p\alpha}$ for $[\text{cov } m]_{jj}^p$ in Equation (4) and
(b) $[\text{cov } m]^c_{jk}{}^\alpha$ for $[\text{cov } m]^c_{jk}$ in Equation (8).

The superscript "$\alpha$" does not apply to the ratios, i.e., "$f_j^p$", because a set of test ratios $S_f = \{f^p\}$ may be selected, to be used with any component j and independent of the data. Although the set $S_f$ does not depend on "j", the choice of optimal ratio $f_j^{p(j)} \in S_f$ can vary with component j, necessitating the use of "j" in the Equations. In Equation (8), the index $\alpha$ now indexes the data to be inverted and not just the test data that were used in the above procedure.

Another exemplary procedure for optimization of cov m is based on information content of the data. Specifically, independent external ionospheric data (e.g., ionosonde measurements). coincident with the 83.4 nm disk data, can provide the basis for determining the information content of the O II 83.4 nm disk measurements. A statistical comparison of the external data with the results of inversions that evaluate only a selected subset of the parameters $N_{max}$, $z_{max}$, and $H_0$ (and if included, $H_1$) allows an optimal subset of parameters (i.e., a subset of components of m) to be determined for retrieval. For convenience in the remaining discussion, assume that $H_1$ remains fixed at zero (or is not selected as a parameter to be varied as part of m).

To limit the inversion to only a desired subset, e.g. $m_2$ (or $z_{max}$), very small values may be selected for the other components of [cov m], e.g., [cov m]$_{11}$ and [cov m]$_{33}$, thereby forcing the algorithm to return the a priori values of those components (parameters that are not in the subset).

For example, tests of the algorithm using actual disk values from a satellite sensor show that a retrieval of the subset containing only $z_{max}$ from disk data can return a wide range of results (F-region peak height values) depending on the tightly constrained a priori values selected for $N_{max}$ and $H_0$. In that example, realistic a priori values $<m_1>$ and $<m_3>$ resulted in a more acceptable retrieved value of $z_{max}$.

Part of the invention then, is to use external data, when available, to evaluate the quality of retrievals which evaluate only a subset of the available model parameters. In such retrievals, the remaining parameters are constrained to realistic a priori values by setting the corresponding components of cov m to very small values. Investigating all possible model parameter subsets in this way will reveal the subset for which the disk measurements provide the most information.

Returning to the exemplary sequence of operations in accordance with the present invention, $\chi^2(m, d^o(t_i), <m>_i)$ is then defined. The values of $d^o(t_i)$ and $<m>_i$ are ingested into Equation (2), along with cov m, cov $d^o$, and cov G an the forward model G(m), to define the value function to be minimized numerically.

For each value of i (i.e., for each disk observation), $\chi^2(m, d^o(t_i), <m>_i)$ is minimized to yield $m^s_i$, the solution.

Finally, the solution: $m^s_i$ is outputted.

An exemplary embodiment of the present invention was tested and will now be discussed. In this discussion, and only this discussion, the indexing convention of the Interactive Data Language™ or IDL™ is assumed. Model parameter indices, (i.e., indexing of components of m) will begin with 0 rather than 1. Thus the index $j \in \{0, 1, 2, 3, 4\}$ corresponds to [$N_{max}$, $z_{max}$, $H_0$, $H_1$, $\kappa$], where $\kappa$ is the scalar of the entire model intensity profile, when selected for use in the solution procedure. Component 3 of m, or $H_1$, will remain fixed at 0 in all tests reported below.

The tests used data on the singly-ionized atomic oxygen 83.4 nm triplet emission, denoted by O II 83.4 nm, from a DMSP F16 SSULI sensor, for the observation date Jan. 8, 2004. The largest observation zenith angle (approximately 119.373°) of the sensor corresponded to a line of sight which intersected the Surface of the Earth. Because of the optical path length of the 83.4 nm emission, this datum has characteristics appropriate for the test.

For reference data and a diagram on inversion of the entire limb intensity profile was included. The ranges of tangent point latitude and longitude for this profile were, respectively, −25.3021 to −36.1582 degrees latitude and 27.8061 to 25.8363 degrees longitude. The latitude and longitude of the disk value used in the tests were, respectively, −28.5077 and 27.5544 degrees. The range of UT values for the profile was 20876.0 to 20966.0 s, with the earliest time corresponding to the selected disk value.

The profile corresponded to a temporally and spatially near-coincident ionosonde measurement from a set of possible coincidences identified for the DMSP orbits on Jan. 8, 2004. The ionosonde resides at Grahamstown, South Africa with the following specifications and data:

| Lat[1] | Lon[1] | Date* | UT[1*] | foF2 (MHz) | HmF2 (km) | TEC Un | SZA | CTD[#] (km) | 2H$_0$ (km) | URSI ID | StaName |
|---|---|---|---|---|---|---|---|---|---|---|---|
| −33.3 | 26.5 | Jan. 8, 2004 | 0600 | 5.525 | 291.5 | 13.012 | 60.0 | 48.1 | 79.8 | GR13L | Grahamstown |

[1]Latitude and Longitude are within range of SSULI scan values and time (UT) is within 734 s.
*The date and time correspond to the ionogram measured at Grahamstown
[#]CTD = Minimum Cross-Track Distance between ionosonde and SSULI track The parameterized ionosphere profile followed Equation (1), with the set of three retrieved parameters [$N_{max}$, $z_{max}$, $H_0$]. For the actual retrievals scalar variables $m_j$, j=0, 1, 2 and constant "base" values [$N^b_{max}$, $z^b_{max}$, $H^b_0$] were defined such that the model parameter values are $N_{max} \equiv m_0 N^b_{max}$, $z_{max} \equiv m_1 z^b_{max}$, $H_0 \equiv m_2 H^b_0$. Thus the inversion procedure varies the values of the scalars {$m_j$} to minimize $\chi^2$, and for the purposes of discrete inverse theory (i.e., Equation (2)), m is the vector of scalars. The base values for the tests were: $N^b_{max} = 1 \times 10 \neq cm^{-3}$, $z^b_{max}=350$ km. $H^b_0=60$ km, $H^b_1=0$, and $\kappa^b=1$. The initialization of the parameters for the Levenberg-Marquardt $\chi^2$ minimization procedure were $m_j=1$ for j=0, 1, 2, implicitly for 3 (although immaterial), and also for j=4 when a limb inversion (Tests 17-19) included the evaluation of a scalar of the theoretical forward intensity profile. The notation for the solution (final values of m) is $m^s$.

The table below shows results of the minimization for various choices of a priori model parameter values <m> and the associated diagonal covariance matrix, cov m. Because cov m is diagonal, only the vector containing the diagonal elements [cov m]$_{jj}$, j=0, 1, 2 was specified.

The corresponding ionosonde values are $m^{iono}$=[0.395, 0.83, 0.665]. The value of $m_2$ is the value given for the scale height "at the F2 peak" or at z=hmF2. This number, is in the range of reasonable top side scale heights but is not necessarily meaningful for an ionosonde, which cannot measure a top side scale height directly.

Table of Demonstration Test Results[†]

| Test | cov m | | | <m> | | | $m^s$ | | |
|---|---|---|---|---|---|---|---|---|---|
| | 0 | 1 | 2 | 0 | 1 | 2 | 0 | 1 | 2 |
| 1 | 40.0 | 40.0 | 40.0 | 0.7 | 0.8 | 1.0 | 0.639893 | 0.658091 | 0.945041 |
| 2 | 4.0 | 4.0 | 4.0 | 0.7 | 0.8 | 1.0 | 0.638363 | 0.658225 | 0.947629 |
| 3 | 0.4 | 0.4 | 0.4 | 0.7 | 0.8 | 1.0 | 0.639005 | 0.659573 | 0.948365 |
| 4 | 0.04 | 0.04 | 0.04 | 0.7 | 0.8 | 1.0 | 0.644943 | 0.671972 | 0.955061 |
| 5 | 0.004 | 0.004 | 0.004 | 0.7 | 0.8 | 1.0 | 0.673249 | 0.736801 | 0.982588 |
| 6 | 0.004 | 0.004 | 4.0 | 0.7 | 0.8 | 1.0 | 0.699623 | 0.799204 | 0.514604 |
| 7 | 0.4 | 0.4 | 4.0 | 0.7 | 0.8 | 1.0 | 0.671213 | 0.719296 | 0.732921 |
| 8 | 4.0 | 4.0 | 40.0 | 0.7 | 0.8 | 1.0 | 0.671136 | 0.718998 | 0.731741 |
| 9 | 0.04 | 4.0 | 400. | 0.7 | 0.8 | 1.0 | 0.699962 | 0.791549 | 0.525434 |
| 10 | 4.0 | 4.0 | 0.00004 | 0.7 | 0.8 | 1.0 | 0.626758 | 0.643705 | 0.999999 |
| 11 | 0.00004 | 4.0 | 0.00004 | 0.7 | 0.8 | 1.0 | 0.699999 | 0.611631 | 0.999999 |
| 12 | 0.00004 | 4.0 | 0.00004 | 0.395 | 0.83 | 0.665 | 0.395014 | 1.04701 | 0.665008 |
| | | | | Reference Limb Inversions | | | | | |
| 13 | 0.00004 | 4.0 | 0.00004 | 0.395 | 0.83 | 0.665 | 0.411993 | 0.959904 | 0.675264 |
| 14 | 4.0 | 4.0 | 4.0 | 0.395 | 0.83 | 0.665 | 0.764115 | 0.685965 | 0.770607 |
| 15 | 4.0 | 4.0 | 4.0 | 0.7 | 0.8 | 1.0 | 0.631314 | 0.734264 | 0.773009 |
| 16[1] | 0. | 0. | 0. | | | | 0.864844 | 0.655684 | 0.767516 |
| 17*[#1] | 0. | 0. | 0. (0. 0.) | | | | 0.937721 | 0.428571 | 0.921017 |
| | | | | | | | $m^s_3$ = 1.00000 | $m^s_4$ = 0.848089 | |
| 18[#] | 0.04 | 0.04 | 4.0, (0. 4.0) | 0.7 | 0.8 | 1.0 (0.0 1.0) | 0.570019 | 0.561005 | 0.913565 |
| | | | | | | | $m^s_3$ = 1.00000 | $m^s_4$ = 0.858266 | |
| 19[#] | 0.04 | 0.04 | 4.0 (0. 4.0) | 0.7 | 1.0 | 1.0 (0.0 1.0) | 0.413031 | 0.728322 | 0.857634 |
| | | | | | | | $m^s_3$ = 1.00000 | 0.855078 | |

[†]Numbers appearing in the second line of the table are indices of components of the respective vectors.
*Stopped when lower constraint on $m_0$ was reached
[#]Inversion includes evaluation of an intensity scalar $m_4$ along with $m_0$, $m_1$, and $m_2$. Parentheses enclose ([cov m]$_{33}$, [cov m]$_{44}$), (<$m_3$>, <$m_4$>). Note that [cov m]$_{33}$ = 0 and <$m_3$> = 0, indicating that the linear scale height parameter $H_1$ is maintained at the input value, which here is zero.
[1]No a priori data, by convention the cov m input to the inversion code is [0., 0.. . . . , 0.]

Figure 5:
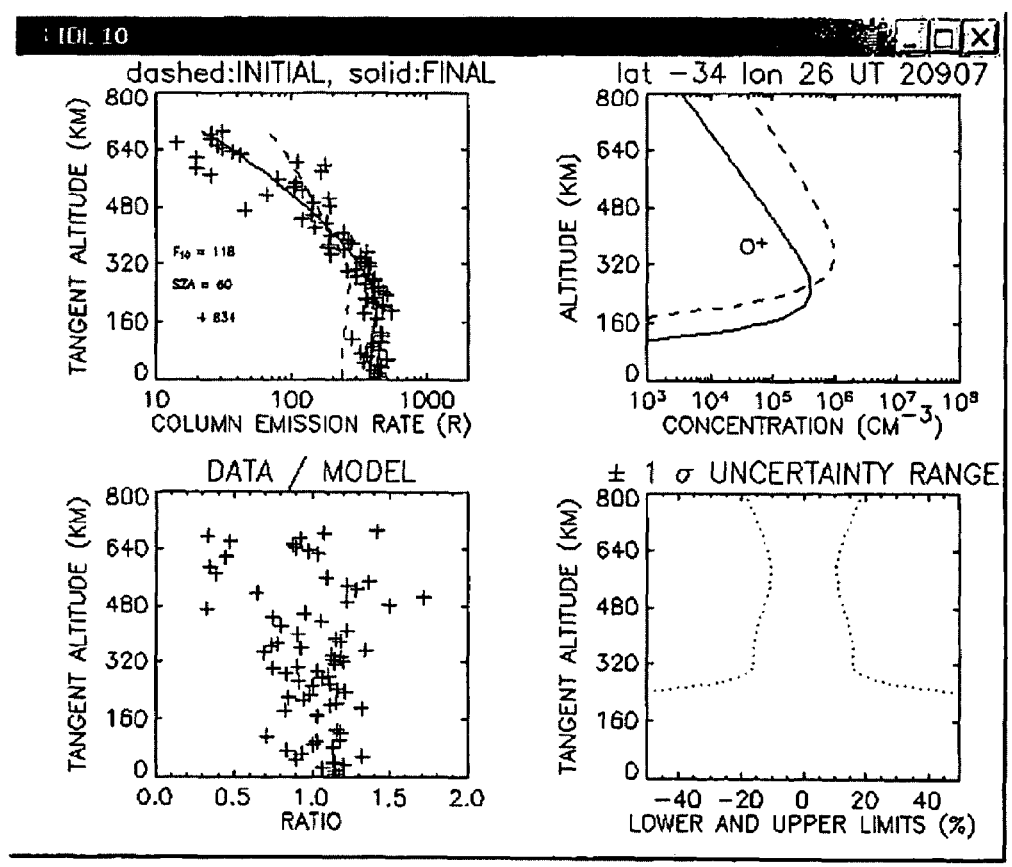
FIG. 5 illustrates an ionospheric profile solution, from a reference inversion of an 83.4 nm limb intensity profile for comparison to an exemplary method.

FIG. 5 provides an example of the appearance of an ionospheric profile solution, in this case for Test 19 above. The upper left panel shows the DIMSP F16 SSULI limb data ("+") as a function of tangent height, the initial model profile (dashed line) and the final fit to the limb intensity profile (solid line) corresponding to the ionospheric profile solution. The upper right diagram shows the initialization for the ionospheric profile (dashed line), which determines the initial model limb intensity profile in the upper left panel. The solid line in the upper right panel gives the ionospheric profile solution, which, along with $m_4$, determines the final limb intensity profile in the upper left panel. The ratio of the data values to the final model intensity values appears in the lower left panel and the associated uncertainty in the ionospheric profile solution appears as the dotted line in the lower right panel.

The "disk" value used in the above tests (1-12) occurs at a negative tangent height, i.e., below a tangent height of 0 km and therefore does not appear in FIG. 5. This "disk" value is similar to the lowest point of the plot in the upper left panel (at a tangent altitude just above 0 km) because of the optical depth of the O II 83.4 nm emission, which limits the lowest altitude from which photons may be observed at the height of DMSP F16 (approximately 830 km, well above the F-region peak).

Referring to the above table of test results for selected values of [cov m] (diagonal components), <m>, and $m^s$, tests 1-12 inverted only the selected disk datum. Tests 1-11 used the same a priori parameter values while Test 12 used values identical to the previously discussed ionosonde data. Generally, all components of the solution differed from the a priori values, except for Tests 10-12, for which some components (labeled by "j") had such low values of [cov m]$_{jj}$ that the corresponding solution components were forced to be essentially identical with the a priori value.

Tests 1-12 demonstrate that the datum is influencing the solution, since the solution differs noticeably from the a priori value <m> when the elements of cov m are sufficiently large.

Tests 1-12 verify the assumption underlying the systematic procedures discussed above for selecting cov m. That is, as each component [cov m]$_{jj}$ decreases in magnitude, the data influence decreases, and conversely, as each component of the covariance increases beyond 0.04 (i.e., for tests 1-3), the successive change in the data influence (Equation (7)) is approximately zero. This demonstrates that one of the systematic procedures discussed above, if applied to these sample tests, will produce values [cov m]$_{00}$≈[cov m]$_{11}$≈[cov m]$_{22}$≈0.04, working as described to choose cov m for maximum data influence and minimum size. A person is free to define cov m by assigning a larger than "optimal" variance for any component of <m>.

The relative values of the components of cov m will affect the data influence of each component. For example, see Test 7, for which the data influence of components me and ml was less than that of $m_2$, whose a priori value <$m_2$> had the larger covariance component, causing $m_2$ to be less constrained in the solution search.

The largest data influence of a particular component $m_i$ occurred when the remaining components (j≠i, k≠i) were forced by very small covariance components to equal the a priori values <$m_j$> and <$m_k$>. See for example Tests 11 and 12.

The reference limb inversions with a priori data (e.g., Test 15) gave similar results for $N_{max}$ ($m_0$) and $z_{max}$ ($m_1$) to the inversion of the single disk value with the same a priori data and cov m (e.g., Test 2), indicating that the single disk datum provided similar information on those parameters. Note that the scale height $H_0$ ($m_2$) solutions differ for Tests 2 and 15 because the limb profile provides independent, specific information on the shape of the ionosphere profile, i.e., the scale height, whereas the disk datum does not. Tests 12 (disk) and 13 (limb) gave very similar results, again when the same <m> and [cov m] were used. Here the scale height solutions were similar because that component of [cov m] was chosen to be so small.

Retrieval of only $z_{max}$ by setting [cov m]$_{00}$ and [cov m]$_{22}$ to very small values in order to tightly constrain $m^s_0$≈<$m_0$> and $m^s_2$≈<$m_2$>, where <$m_0$> and <$m_2$> are known to be realistic, might produce more realistic values of $m^s_1$ or, equivalently, the solution $z_{max}^s = m^s_1 \cdot (350$ km$)$ in the above tests.

Regarding paragraph [0101], Tests 11 and 12 provide some evidence of the potential advantage of setting [cov m] so that only a subset of the retrieved parameters $\{m^s_j\}$ differ from the a priori values >m>, as discussed above. Test 11 used tightly constrained a priori values <$m_0$>=0.7 and <$m_2$>=1.0, which differed from the respective near-coincident ionosonde values 0.395 and 0.665. The result was $m^s_1$=0.61 or $z_{max}^s$= 213 km, a very low ionosphere (and 79 km lower than the ionosonde value of 292 km). When the ionosonde values of parameters 0 and 2 were used as a priori data, i.e., <$m_0$>=0.395 and <$m_2$>=0.665, the inversion of the disk datum produced $m^s_1$=1.04 or $z_{max}^s$=364 km, which is in the same qualitative peak height range as the ionosonde value and closer to the latter. The important thing here is that lower, tightly constrained a priori values <$m_0$> and <$m_2$>, resulted in a significantly higher value of $m^s_1$, which is the behavior expected from physics. A better estimate of the scale height $H_0$ than the highly inaccurate value inferred from the ionosonde would produce better agreement of $z_{max}^s$ with the ionosonde value, "$z_{max}^{iono}$". A greater improvement in $m^s_1$ might also result from using a less restrictive value of [cov m]$_{22}$ so that $m^s_2$ could differ from <$m_2$>. This is an example of setting [cov m] to force the retrieval of subsets of the parameter vector m to determine the useful information content of a disk-viewing data set for O II 83.4 nm, as described above.

The foregoing description of various preferred embodiments of the invention have been presented for purposes of illustration and description. It is not intended to be exhaustive or to limit the invention to the precise forms disclosed, and obviously many modifications and variations are possible in light of the above teaching. The exemplary embodiments, as described above were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A method comprising:

detecting a first intensity of 83.4 nm airglow from singly charged oxygen ions ($O^+$) along a vector from Earth to a satellite above the ionosphere;

obtaining a first altitude at which the number density of singly charged oxygen ions ($O^+$) peaks in the F-region of the ionosphere along the vector from Earth to the satellite;

obtaining a first peak singly charged oxygen ion ($O^+$) number density in the F-region of the ionosphere along the vector from Earth to the satellite;

obtaining a first atomic oxygen scale height in the F-region of the ionosphere along the vector from Earth to the satellite;

estimating a second altitude at which the number density of singly charged oxygen ions ($O^+$) peaks in the F-region of the ionosphere along the vector from Earth to the satellite;

estimating a second peak singly charged oxygen ion ($O^+$) number density in the F-region of the ionosphere along the vector from Earth to the satellite;

estimating a second atomic oxygen scale height in the F-region of the ionosphere along the vector from Earth to the satellite;

estimating an amount of singly charged oxygen ions ($O^+$) in the F-region of the ionosphere at points along the vector from Earth to the satellite based on the estimated second altitude, the estimated second peak density and the estimated second atomic oxygen scale height;

estimating a second intensity of 83.4 nm airglow from singly charged oxygen ions ($O^+$) along the vector from Earth to the satellite based on the estimated amounts of singly charged oxygen ions ($O^+$) in the F-region of the ionosphere at the points along the vector from Earth to the satellite;

defining a generalized chi-squared function of the first altitude, the first peak density, the first atomic oxygen scale height, the estimated second altitude, the estimated second peak density, the estimated second atomic oxygen scale height, the first intensity and the estimated second intensity;

minimizing the generalized chi-squared function by varying at least one of the estimated second altitude, the estimated second peak density and the estimated second atomic oxygen scale height to determine optimal estimates of the estimated second altitude, the estimated second peak density and the estimated second atomic oxygen scale height; and determining the altitude profile of the amount of singly charged atomic oxygen ions ($O^+$) in the F-region of the ionosphere between the Earth and the satellite based on the optimal estimates of the estimated second altitude, the estimated second peak density and the estimated second atomic oxygen scale height.

* * * * *